(12) United States Patent
Geertsen

(10) Patent No.: US 9,332,903 B2
(45) Date of Patent: May 10, 2016

(54) HEADGEAR FOR OBSERVATION OF EYE MOVEMENTS

(71) Applicant: GN Otometrics A/S, Taastrup (DK)

(72) Inventor: Thomas Geertsen, Slagelse (DK)

(73) Assignee: GN Otometrics A/S, Taastrup (DK)

( * ) Notice: Subject to any disclaimer, the term of this patent is extended or adjusted under 35 U.S.C. 154(b) by 119 days.

(21) Appl. No.: 14/033,312

(22) Filed: Sep. 20, 2013

(65) Prior Publication Data

US 2015/0077712 A1    Mar. 19, 2015

(30) Foreign Application Priority Data

Sep. 19, 2013   (DK) ................................ 2013 70523
Sep. 19, 2013   (EP) ..................................... 13185161

(51) Int. Cl.
*A61B 3/14* (2006.01)
*A61B 3/113* (2006.01)
*A61F 9/02* (2006.01)
*A61F 9/04* (2006.01)

(52) U.S. Cl.
CPC ................. *A61B 3/113* (2013.01); *A61F 9/029* (2013.01); *A61F 9/04* (2013.01)

(58) Field of Classification Search
CPC ....................................................... A61B 3/113
USPC ........................... 351/209, 210, 246, 205, 208
See application file for complete search history.

(56) References Cited

U.S. PATENT DOCUMENTS

| | | | |
|---|---|---|---|
| 4,331,136 A | 5/1982 | Russell et al. | |
| 4,815,839 A | 3/1989 | Waldorf | |
| 4,988,183 A * | 1/1991 | Kasahara et al. | 351/210 |
| 5,070,883 A | 12/1991 | Kasahara | |
| 5,093,567 A * | 3/1992 | Staveley | 250/221 |
| 2002/0138898 A1 | 10/2002 | Chiang | |
| 2004/0218140 A1 | 11/2004 | Bleau | |
| 2005/0193479 A1 | 9/2005 | Atta et al. | |
| 2008/0148461 A1 | 6/2008 | Guyuron et al. | |
| 2009/0303435 A1 | 12/2009 | Flitcroft | |
| 2011/0004969 A1 | 1/2011 | Frohlich et al. | |
| 2011/0085135 A1 | 4/2011 | Bertolli | |
| 2011/0299034 A1 | 12/2011 | Walsh et al. | |

FOREIGN PATENT DOCUMENTS

EP     0 346 846 A1   12/1989
JP     2006235139     9/2006
(Continued)

OTHER PUBLICATIONS

Examination and Search Report dated Jun. 30, 2014 in Danish Application No. PA 2013 70523 (6 pages).
(Continued)

*Primary Examiner* — Hung Dang
(74) *Attorney, Agent, or Firm* — Vista IP Law Group, LLP

(57) ABSTRACT

An apparatus for covering a left eye and a right eye of a human, includes: a first eye piece configured for covering a left eye of a human; and a second eye piece configured for covering a right eye of the human; wherein the first eye piece and the second eye piece are configured for preventing transmission of visible light; and wherein at least one of the first eye piece and the second eye piece comprises a region that is transparent for electromagnetic radiation with a wavelength range outside a visible range.

20 Claims, 22 Drawing Sheets

(56) References Cited

FOREIGN PATENT DOCUMENTS

| JP | 2007029207 | 2/2007 |
|---|---|---|
| WO | WO 97/17020 | 5/1997 |

OTHER PUBLICATIONS

Extended European Search Report for EP Patent Application No. 13185161.0 dated Feb. 10, 2014 (7 pages).

First Technical Examination of DK Patent Application No. PA 2013 70523 dated Nov. 7, 2013 (5 pages).

"Cold Mirror CM-05 Transmission Data" Optical-Filters.com, accessed May 29, 2014, http://www.optical-filters.com/Cold_Mirror_CM-05_Transmission_Data.aspx (1 page).

European Communication dated Feb. 19, 2016 for corresponding EP Patent Application No. 13 185 161.0, 5 pages.

* cited by examiner

HEADGEAR FOR OBSERVATION OF EYE MOVEMENTS

RELATED APPLICATION DATA

This application claims priority to and the benefit of Danish Patent Application No. PA 2013 70523, filed on Sep. 19, 2013, pending, and European Patent Application No. 13185161.0, filed on Sep. 19, 2013, pending. The disclosures of both of the above-identified applications are expressly incorporated by reference herein.

FIELD OF TECHNOLOGY

A new apparatus is provided, with two eye pieces each of which is configured to cover a respective one of a human's eyes and thereby prevent visible light from reaching the human's eyes. The eye pieces are transparent for electromagnetic radiation with a wavelength range outside the visible range, e.g. infrared light, and/or ultraviolet light, etc.
Preferably, the new apparatus is disposable.

BACKGROUND

It is well-known to apply video technology to record and quantify eye movements. Typically, when eye movements are recorded, the human wears video goggles with a small infrared camera whereby one eye of the human, typically the right eye, is located within the viewing field of the camera, e.g. using a mirror to deflect infrared light from the eye into the camera.

Video goggles with two infrared cameras for recording eye movements of both eyes are also known.

For some measurements, prior art video goggles seek to prevent visible light from reaching the human's eyes in order to avoid suppression of reflex eye movements, for example nystagmus, due to optic fixation of the human's eyes. Thus, prior art video goggles desirably provide a complete light proof seal around its circumference when worn by the human so that no visible light is allowed to pass through the seal. The eyes of a human are extremely light sensitive, especially after having accommodated to darkness for a while so that light, even at very low intensities, illuminating the interior of the video goggles may undesirably suppress reflex eye movements.

The required light proof seal is difficult to obtain with prior art video goggles that are intended to be used by different humans with different facial anatomy and often, doctors prefer to study eye movements in a dark room despite the fact that this makes the study much more cumbersome to perform.

The prior art video goggles also require proper cleaning between use by different humans.

SUMMARY

In order to overcome the above-mentioned and other difficulties, an apparatus with two eye pieces is provided that isolates the human's eyes visually from the outside environment so that the human experiences substantially complete darkness. The eye pieces are made opaque to visible light, and each of the eye pieces is configured to form a lightproof seal around the respective eye when worn by the human.

Thus, an apparatus configured for covering a left eye and a right eye of a human is provided, comprising
a first eye piece configured for covering the left eye of the human, and
a second eye piece configured for covering the right eye of the human, and wherein
the first eye piece and the second eye piece are configured for preventing transmission of visible light, and wherein
at least one of the first eye piece and the second eye piece comprises a region that is transparent for electromagnetic radiation with a wavelength range outside a visible range.

Throughout the present disclosure, the first eye piece may be termed the left eye piece and the second eye piece may be termed the right eye piece.

At least one of the first eye piece and the second eye piece has a region, e.g. a window, that is transparent for electromagnetic radiation with wavelengths outside the visible range, i.e. electromagnetic radiation with wavelengths residing outside a visible range from 400 nm-700 nm, such as infrared light, e.g., infrared light ranging from 700 nm-1 mm, such as infrared light ranging from 700 nm-5000 nm, preferably from 740 nm-2000 nm, more preferred from 850 nm to 1100 nm, ultraviolet light, e.g. ultraviolet light ranging from 20 nm-400 nm, such as ultraviolet light ranging from 200 nm-400 nm, preferably from 300 nm to 400 nm, more preferred from 320 nm to 380 nm.

The apparatus with the first eye piece and the second eye piece is intended to be worn by the human underneath separate video goggles, i.e. between the eyes and the video goggles. The video goggles have camera(s) that is/are capable of recording electromagnetic radiation outside the visible range passing through the region, e.g. infrared camera(s), ultraviolet camera(s), etc, for observation of eye movements, such as nystagmus. The video goggles also comprise sources of electromagnetic radiation for illumination of the eye(s) with the electromagnetic radiation outside the visible range, for example infrared light diodes, ultraviolet diodes, etc.

Since darkness is provided by the apparatus with the first eye piece and the second eye piece, the separate video goggles need not be opaque to visible light and in particular do not need to provide a lightproof seal around the eyes of the human, making it much easier to fit the video goggles to humans with different facial anatomy. This also reduces the effort of cleaning the video goggles between uses.

The video goggles may have the form of a helmet or a mask.

Since the first eye piece and the second eye piece prevent visible light from reaching the human's eyes and thereby suppress optic fixation of the human's eyes, the one or more camera(s) need not be arranged in goggles, but may be arranged in another way with the eye(s) for which eye movements, such as nystagmus, are to be observed in the field(s) of view of the camera(s).

The region may have any of various configurations. For example, the region may have a flat anterior surface. In another example, the region may have a curved, convex anterior surface, e.g. for moving a possible reflection of a source of electromagnetic radiation, such as IR LEDs, out of the field of view of a camera used for eye movement recording.

In addition, the region may have various tints or coatings (e.g., an anti-reflection coating), for improved image formation as known in the art.

The region may be made of a material transparent for infrared light, such as an acrylic material, such as the infrared transparent material PC Makrolon 2405, colour: 450601.

Alternatively, the region may be made of a material that is transparent for visible light; however coated with a material that is opaque to visible light. The coating may be the so-called Cold Mirror CM-05 material, see http://www.optical-filters.com/Cold Mirror CM-05 Transmission Data.aspx.

The region may have a transmittance, i.e. the fraction of incident electromagnetic radiation at a specified wavelength that passes through the region, of more than 50%, preferably more than 60%, more preferred more than 70%, most preferred more than 80% of infrared light in the wavelength range from 850-1100 nm.

The region and the light proof seal in combination may have a transmittance of less than 1% of visible light in the wavelength range from 380 nm-740 nm.

Each of the first eye piece and the second eye piece may be made of a material that is opaque to visible light. The material may be a plastic material, such as a soft plastic material, or a hard plastic material, such as a standard hard black plastic.

The at least one eye piece with the region may comprise a frame with an aperture for accommodation of the region, e.g. a window, and made of another material than the material of the region, such as a plastic material, such as a soft plastic material, or a hard plastic material, such as a standard hard black plastic.

Alternatively, the eye piece with the region may be made of the material of the region so that the frame and region constitute a single part.

Both eye pieces may be made of the material of the region.

At least one of the first eye piece and the second eye piece may comprise a peripheral flange that is shaped to conform to an area surrounding the respective eye, e.g., an area at and approximate an orbital rim of the respective eye.

Preferably, the first eye piece and the second eye piece are not interconnected with each other, e.g. by a head strap and/or a nose strap or nose piece, so that each of the eye pieces can be mounted at the eye of the human individually and independent of the mounting of the other eye piece, for prevention of visible light from reaching the eyes. The individual and independent positioning of the first eye piece and the second eye piece makes it easier to establish a lightproof seal around the human's eyes with standard sized and standard shaped eye pieces, i.e. eye pieces that are not customized to individually fit the facial anatomy of a specific human.

Preferably, at least one of the first eye piece and the second eye piece is retained against the human's face using an adhesive applied to the at least one of the first eye piece and the second eye piece, e.g. the at least one of the first eye piece and the second eye piece may have an adhesive surface intended for attachment to a skin surface.

Preferably, both the first eye piece and the second eye piece are retained against the human's face using an adhesive applied to the eye pieces, e.g. the eye pieces may have adhesive surfaces intended for attachment to a skin surface.

The surface intended for attachment to a skin surface preferably includes a layer of a flexible material, such as polyethylene foam, silicone, molded TPE, etc, to provide a sealing surface that better accommodates uneven facial surfaces.

The adhesive surface may reside on the flexible material.

The adhesive may be a gentle acrylic adhesive for skin adhesion.

The adhesive surface may comprise a layer of an adhesive tape, such as MSX-6674C which is a double coated synthetic rubber/gentle acrylic adhesive tape designed for medical applications supplied by 3M Medical Specialties, that is secured to the at least one of the first eye piece and the second eye piece.

The flexible material may be included in the adhesive tape.

The adhesive may be part of a double-sided adhesive tape, the double-sided tape having an additional adhesive surface adhering to a posterior surface of the at least one of the first eye piece and the second eye piece.

Preferably, the double-sided tape is discarded after use so that the requirement of cleaning eye pieces between uses is reduced.

Attachment to a facial skin surface with an adhesive facilitates formation of a lightproof seal between the eye pieces and the skin surface. Since skin is flexible, skin adhering to the eye pieces is capable of staying attached to the adhesive surface even if the adhering surface moves slightly. Thus, pressing an adherent and flexible surface of an eye piece against a facial surface around an eye of a human ensures formation of a lightproof seal. The lightproof seal is maintained when the pressure is relieved even if the adhesive surface does not conform exactly to the relaxed anatomy of the skin surface to which it is attached, since the skin is capable of deforming into the shape of the adhesive surface that approximately conforms to the facial surface around the eye in question.

The apparatus with the first eye piece and the second eye piece may have an interconnecting nose piece or nose strap, e.g. connected to nasal end portions of the eye pieces while not having an interconnecting head strap.

The apparatus with the first eye piece and the second eye piece may have an interconnecting nose piece or nose strap, e.g. connected to nasal end portions of the eye pieces, and an interconnecting head strap.

The head strap may be elastic or may be adjustable or both. The apparatus with the first eye piece and the second eye piece interconnected with a head strap may not have an adhesive surface.

At least one of the first eye piece and the second eye piece may comprise a transversal portion that is positioned in front of one of the eyes when worn by the human, and an annular peripheral wall that extends around the transversal portion and rearwardly there from, and a peripheral flange connected to the peripheral wall and shaped to conform to the shape of the eye surroundings.

A method of determining an eye movement is provided, comprising the steps of:
providing an apparatus having
a first eye piece a second eye piece, and
a camera, wherein
at least one of the first eye piece and the second eye piece comprises a region that is transparent for electromagnetic radiation with a wavelength range outside a visible range;
preventing visible light from reaching eyes of a human using the first eye piece and the second eye piece; and
tracking a movement of at least one of the eyes using the camera.

A method of determining an eye movement is also provided, comprising the steps of
mounting an apparatus with the first eye piece and the second eye piece as disclosed above on the head of a human for preventing visible light from reaching the eyes of the human,
mounting one camera so that one eye of the human resides within the field of view of the camera,
tracking eye movements with the camera, and
discarding at least part of the apparatus with the first eye piece and the second eye piece.

Preferably, the eye pieces are discarded after use with the same human, whereby the requirement of cleaning the eye pieces between uses with different humans is eliminated.

An apparatus for covering a left eye and a right eye of a human, includes: a first eye piece configured for covering a left eye of a human; and a second eye piece configured for covering a right eye of the human; wherein the first eye piece and the second eye piece are configured for preventing transmission of visible light; and wherein at least one of the first eye piece and the second eye piece comprises a region that is transparent for electromagnetic radiation with a wavelength range outside a visible range.

Optionally, the first eye piece and the second eye piece are unconnected for individual and independent positioning at the respective left and right eyes.

Optionally, at least one of the first eye piece and the second eye piece comprises an adhesive surface for adhesively securing the at least one of the first eye piece and the second eye piece to a skin surface of the human.

Optionally, the adhesive surface is on a flexible material.

Optionally, the adhesive surface comprises a layer of adhesive tape that is secured to the at least one of the first eye piece and the second eye piece.

Optionally, the adhesive surface is a part of a double-sided tape, the double-sided tape having an additional adhesive surface adhering to a posterior surface of the at least one of the first eye piece and the second eye piece.

Optionally, the region that is transparent for electromagnetic radiation with a wavelength range outside the visible range, is made of a material that is transparent for visible light coated with a material that is opaque to visible light.

Optionally, the region that is transparent for electromagnetic radiation with the wavelength range outside the visible range comprises at least a portion of a surface that covers the left eye or the right eye.

Optionally, the at least one of the first eye piece and the second eye piece with the region that is transparent for electromagnetic radiation with the wavelength range outside the visible range, comprises a frame with an aperture for accommodation of a window that defines the region, the frame being made of a material that is different from a material of the window.

Optionally, at least one of the first eye piece and the second eye piece comprises a peripheral flange that is shaped to conform to a shape of an orbital rim of the left eye or the right eye.

Optionally, at least one of the first eye piece and the second eye piece comprises a transversal portion that is positioned in front of one of the eyes when worn by the human, and an annular peripheral wall that surrounds the transversal portion and extends rearwardly therefrom, and a peripheral flange surrounding the peripheral wall and shaped to conform to a shape of an orbital rim of one of the eyes.

Optionally, the apparatus further includes a nose piece that interconnects the first eye piece and the second eye piece, and that is configured for fitting across a nose of the human.

Optionally, the apparatus further includes a head strap that interconnects the first eye piece and the second eye piece, and that is configured for fitting around a rear of a head of the human.

Optionally, the region has a transmittance of more than 50% of infrared light in a wavelength range from 850-1100 nm.

A device for worn above a shoulder of a user, includes: a structure; at least one camera coupled to the structure; and the apparatus; wherein the first eye piece and the second eye piece of the apparatus are coupled to the structure.

Optionally, the structure comprises a helmet.

Optionally, the structure comprises a mask.

Optionally, the structure comprises a frame of a glasses or goggles.

A method of determining an eye movement, includes: providing an apparatus having a first eye piece a second eye piece, and a camera, wherein at least one of the first eye piece and the second eye piece comprises a region that is transparent for electromagnetic radiation with a wavelength range outside a visible range; preventing visible light from reaching eyes of a human using the first eye piece and the second eye piece; and tracking a movement of at least one of the eyes using the camera.

Other and further aspects and features will be evident from reading the following detailed description.

BRIEF DESCRIPTION OF THE DRAWINGS

The drawings illustrate the design and utility of embodiments, in which similar elements are referred to by common reference numerals. These drawings may or may not be drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

In the drawings.

DETAILED DESCRIPTION

Figure 1:
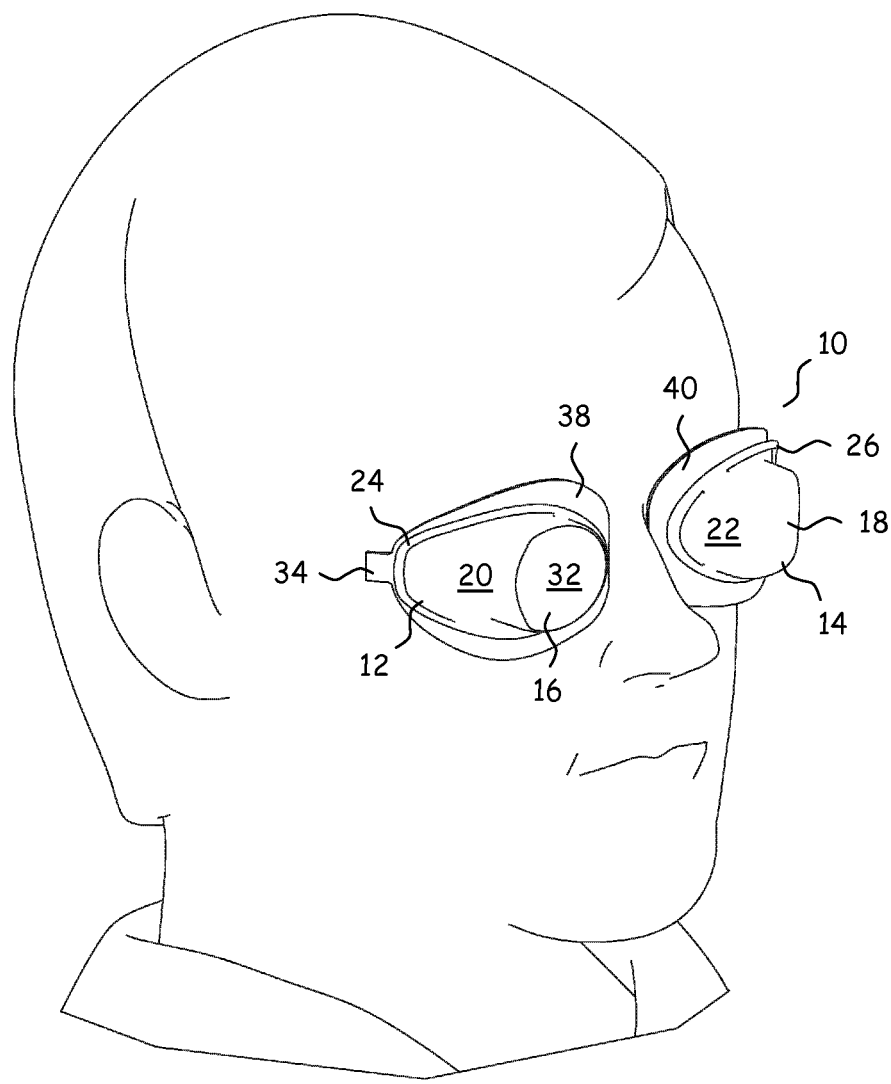
FIG. 1 schematically shows a perspective view of a human's head with an exemplary new set of eye pieces, FIG. 2 schematically shows the human's head from the side with the new set of eye pieces also shown in FIG. 1, FIG. 3 schematically shows an exploded perspective view of the set of eye pieces of FIG. 1 behind video goggles with an IR camera, FIG. 4 schematically shows a perspective view of the set of eye pieces of FIG. 1 behind video goggles with an IR camera, FIG. 5 schematically shows an exploded perspective view of the set of eye pieces of FIG. 1.

Various illustrative examples of the new set of eye pieces, headgear and method according to the appended claims will now be described more fully hereinafter with reference to the accompanying drawings, in which various embodiments of new set of eye pieces, headgear and method are illustrated. The new set of eye pieces; headgear and method according to the appended claims may, however, be embodied in different forms and should not be construed as limited to the embodiments set forth herein. In addition, an illustrated embodiment needs not have all the aspects or advantages shown. An aspect or an advantage described in conjunction with a particular embodiment is not necessarily limited to that embodiment and can be practiced in any other examples even if not so illustrated, or if not so explicitly described. It should also be noted that the accompanying drawings are schematic and simplified for clarity, and they merely show details which are essential to the understanding of the new set of eye pieces, headgear and method, while other details have been left out.

As used herein, the singular forms "a," "an," and "the" refer to one or more than one, unless the context clearly dictates otherwise.

FIGS. 1-7 illustrate one exemplary new apparatus 10 with the first and second eye pieces 12, 14, which comprises separate right and left eye pieces 12, 14, each of which is configured to isolate a respective one of a human's eyes from visible light of the surrounding environment. In the illustrated example, each of the right and left eye pieces 12, 14 comprises a transversal portion 16, 18 for covering an eye and spanning substantially perpendicular to a forward looking direction of the human, when the apparatus 10 with the right and left eye pieces 12, 14 is mounted with the eye pieces 12, 14 in their intended operational position on the human's head. Each of the first and second eye pieces 12, 14 further has a curved annular peripheral wall 20, 22 surrounding and supporting the respective transversal portions 16, 18. The walls 20, 22 have respective flanges 24, 26 with posterior surfaces 28, 30 (shown in FIG. 6) that are configured to be attached to the skin surface of the human at or adjacent the orbital rims.

The right eye piece 12 has a region 32 in its transversal portion 16 that is transparent for infrared light so that observation of the right eye of the human can be performed with an infrared camera. When the eye pieces 12, 14 are mounted in their intended operational positions covering the right eye and left eye, respectively, they form a substantially light proof seal with the face of a wearer and thereby prevent visible light from reaching the wearer's eyes, whereby suppression of eye movements, such as nystagmus, is avoided, due to the fact that the eyes are not presented with an illuminated feature that the line of sight of the eyes can be aligned with.

Each eye piece 12, 14 desirably is constructed from a relatively stiff and hard opaque plastic, with good scratch resistance and optical qualities. A suitable plastic is an impact-resistant polycarbonate material, although various other materials are also usable.

The region 32 is made of a material transparent for infrared light, such as an acrylic material, such as the infrared transparent material PC Makrolon 2405, colour: 450601.

The region 32 of the eye piece 12 can have any of various configurations. In the illustrated eye piece 12, for example, the region 32 includes a flat anterior portion.

Figure 2:
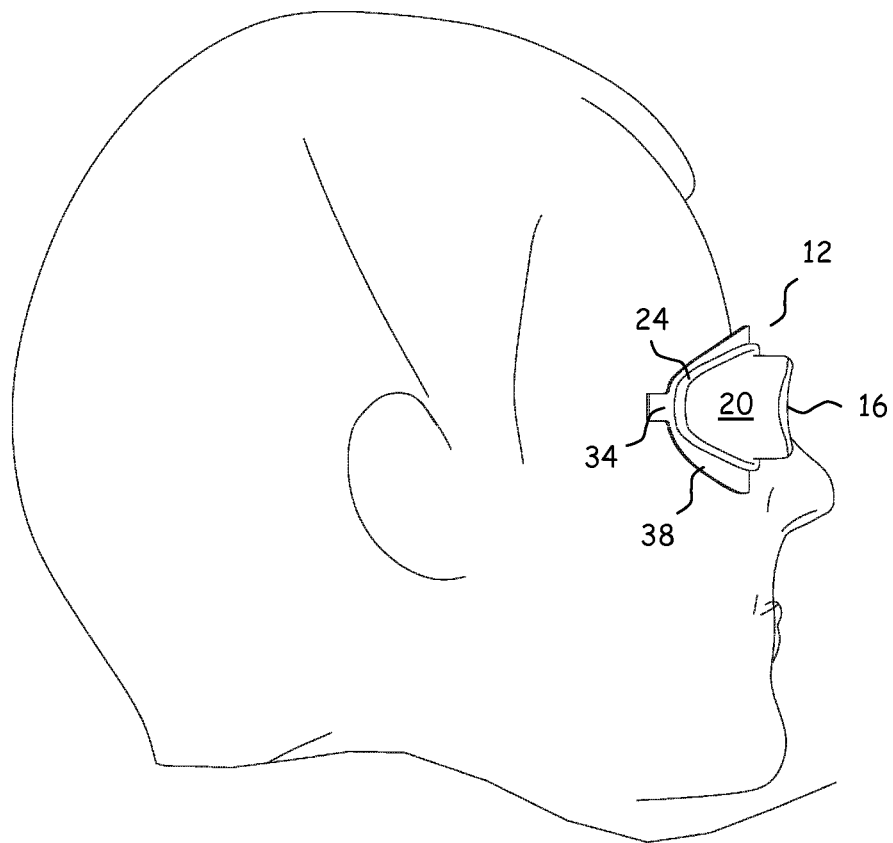
Figure 3:
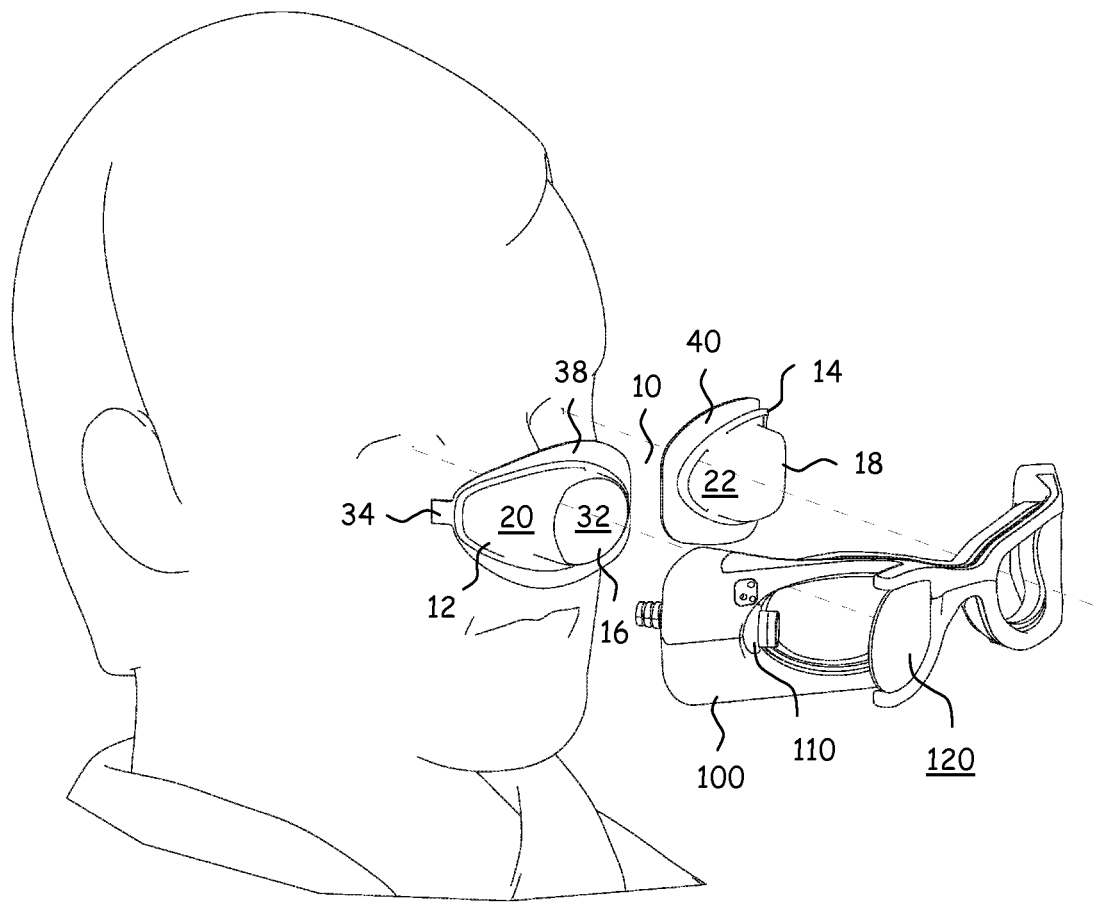

In another example, the region 32 is formed with a curved, convex anterior surface, rather than the flat anterior lens surface shown in FIGS. 1-3, e.g. for moving a possible reflection of a source of infrared light out of the field of view of the infrared camera. In addition, the region 32 can have various tints or coatings (e.g., an anti-reflection coating), for improved image quality as known in the art.

The flanges 24, 26 are sized and shaped such that at least the upper and lower nasal portions of the flanges or portions thereof, can be positioned within the adjacent margins of the orbital rims, or within the outer margins of the orbicularis oculi muscles. The posterior surfaces 28, 30 (shown in FIG. 6) of the upper and lower nasal portions generally seats against soft tissue within the orbital rim, or against the fibers of the orbicularis oculi muscles, and posterior surfaces 28, 30 of the upper and lower temporal portions of the flanges 34, 36 generally seats against the adjacent temporal margins of the orbital rims.

It is not necessary that the entire eye piece fit within the orbital rim or be engageable by the orbicularis oculi muscles. It is possible, for example, that the muscles only engage and retain a portion (such as a nasal or temporal portion) of the eye piece.

In addition, the wearer can affect the exact positioning of the eye pieces 12, 14 with respect to the orbital rims. For example, by angling the transversal portions 16, 18 slightly downwardly with respect to the normal line of sight, a wearer can position an eye piece such that the upper nasal portion the lower nasal portion and the lower temporal portion except for the temporal ends 34, 36 are positioned within the orbital rim. In addition, the positioning of the flanges 24, 26 relative to the orbital rims can vary slightly depending on the facial morphology of the wearer.

In an alternative embodiment, the flanges 24, 26 can be sized and shaped to fit substantially or entirely within the orbital rims. In another alternative embodiment, the flanges 24, 26 can be sized and shaped to reside completely outside the orbital rims.

Dimensions of the eye pieces 12, 14 may be determined using many different approaches. For example, the first and second eye pieces 12, 14 can be custom designed and fitted to a particular individual. Preferably, the dimensions can be determined by reference to a standard head form that has been designed according to statistical norms from the population, or from published texts and descriptions of such norms.

In the illustrated right eye piece 12, the region 32 and the transversal portion 16 are separately formed from different materials and then subsequently joined together to form the eye piece 12.

The region 32 can be either permanently attached to the transversal portion 16 or connected to the transversal portion in a removable manner.

In another apparatus 10 with the first and second eye pieces 12, 14, each eye piece 12, 14 has a one-piece or unitary construction.

Figure 6:
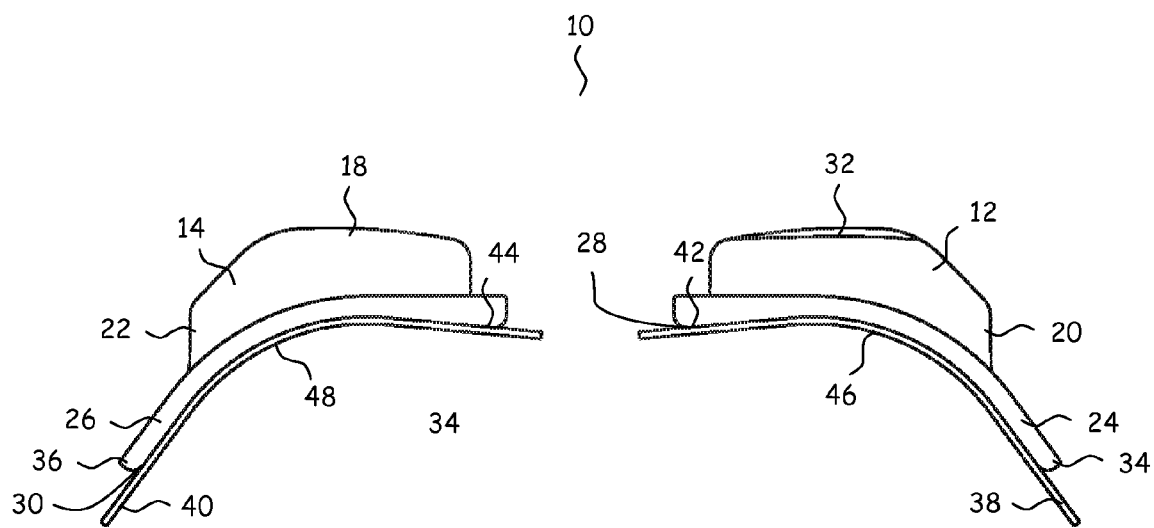
FIG. 6 is a top view of the set of eye pieces shown in FIG. 1.
Figure 7:
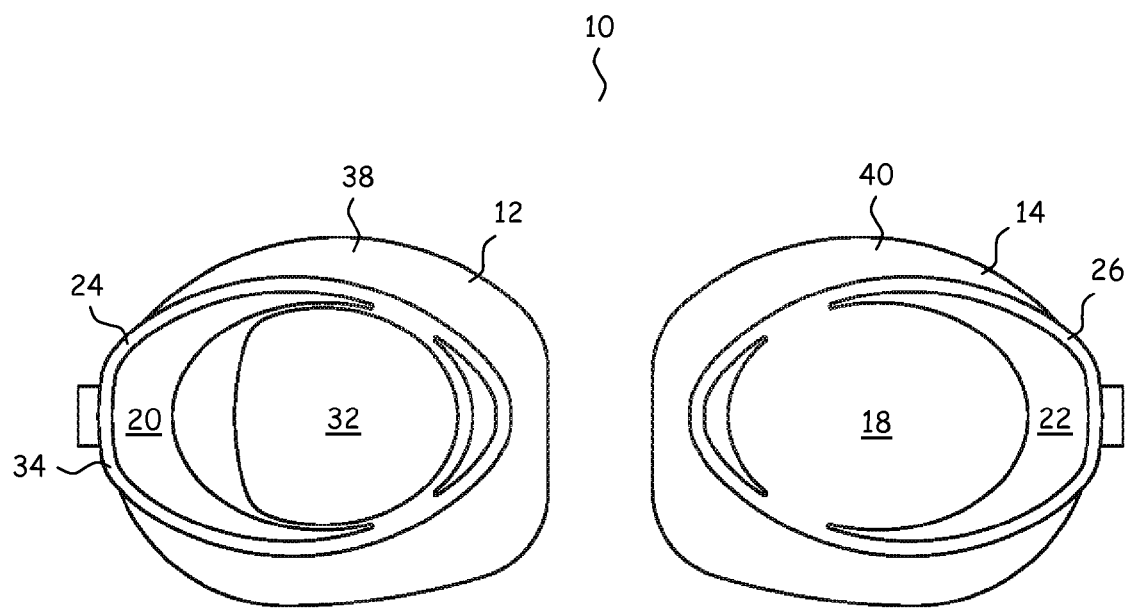
FIG. 7 is a front view of the set of eye pieces shown in FIG. 1, FIG. 8 schematically shows a perspective view of a human's head with another exemplary new set of eye pieces, FIG. 9 schematically shows the human's head from the side with the new set of eye pieces of FIG. 8, FIG. 10 schematically shows an exploded perspective view of the set of eye pieces of FIG. 8 behind video goggles with an IR camera, FIG. 11 schematically shows a perspective view of the set of eye pieces of FIG. 8 behind video goggles with an IR camera, FIG. 12 schematically shows an exploded perspective view of the set of eye pieces of FIG. 8.
Figure 8:
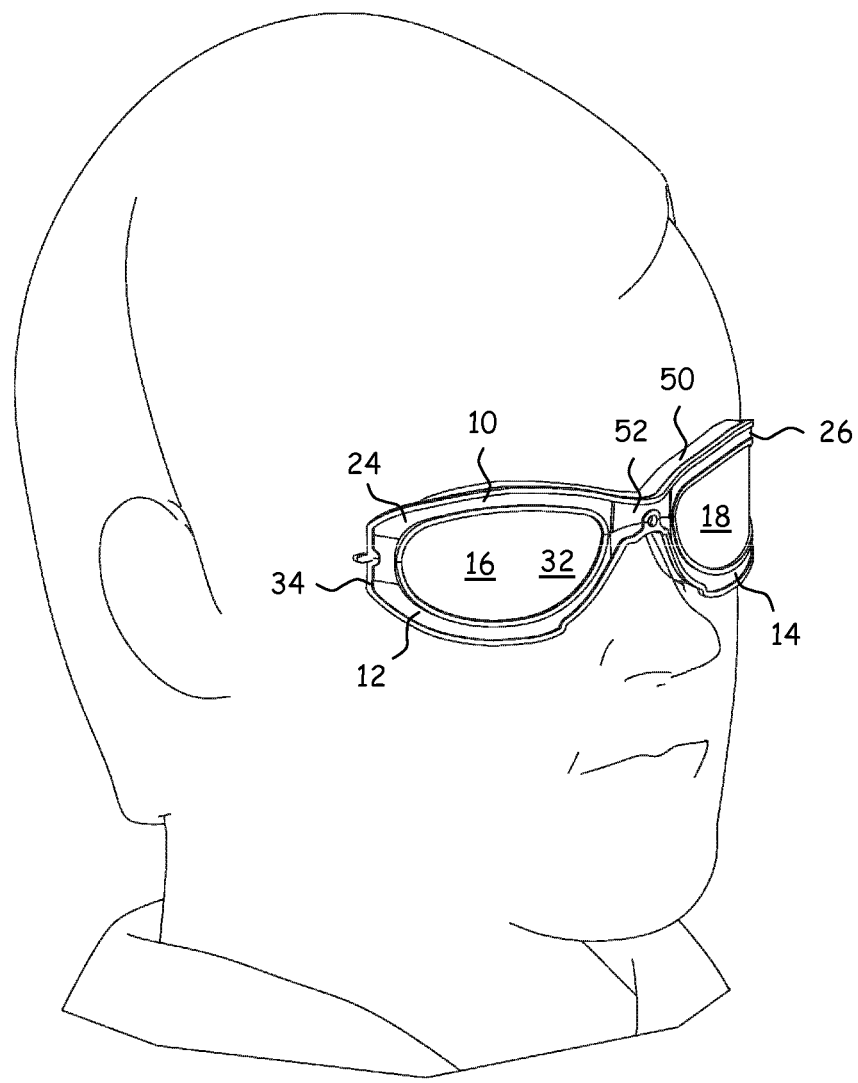
Figure 9:
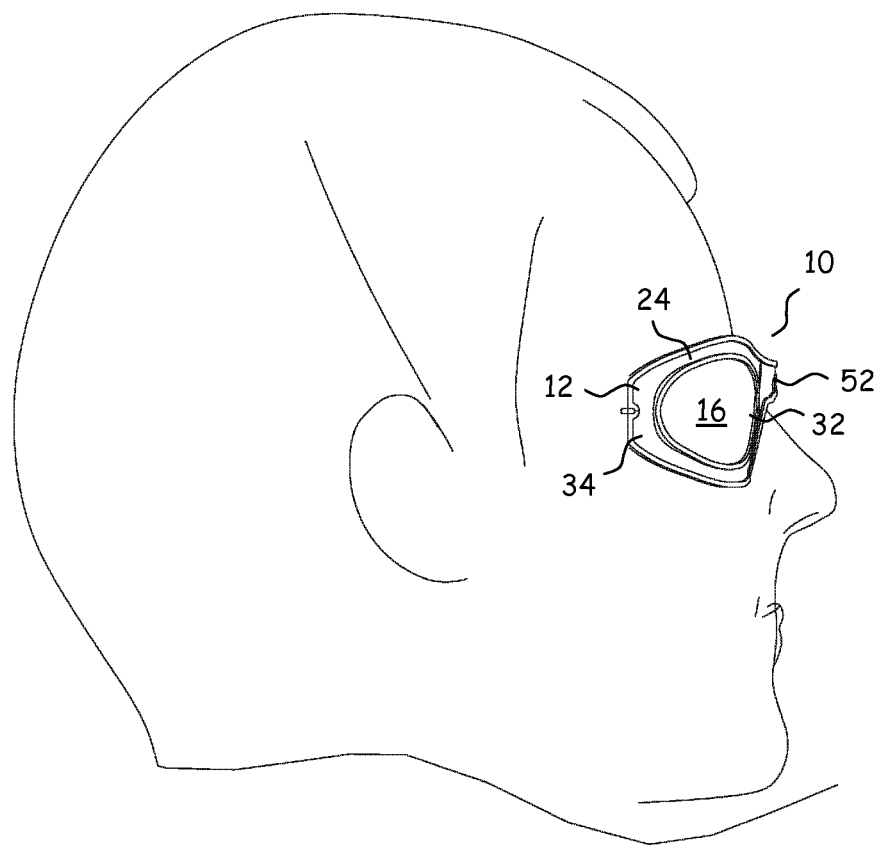
Figure 10:
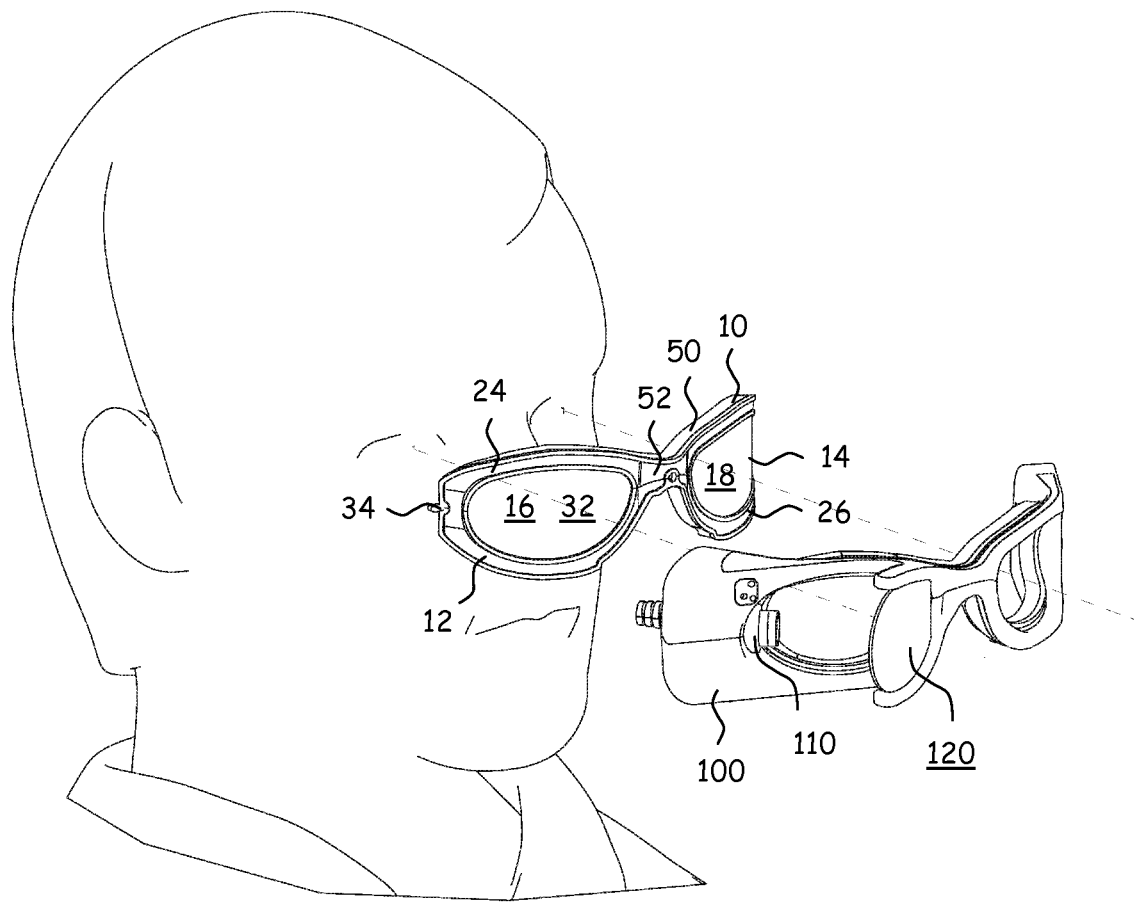
Figure 11:
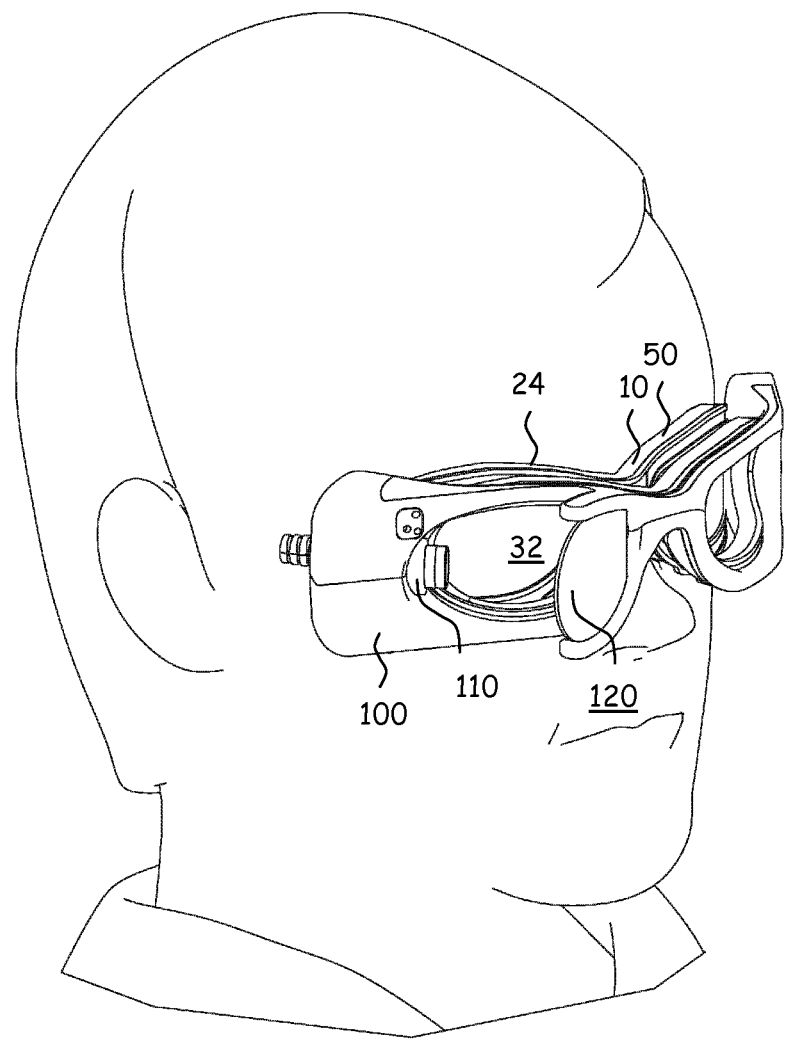
Figure 12:
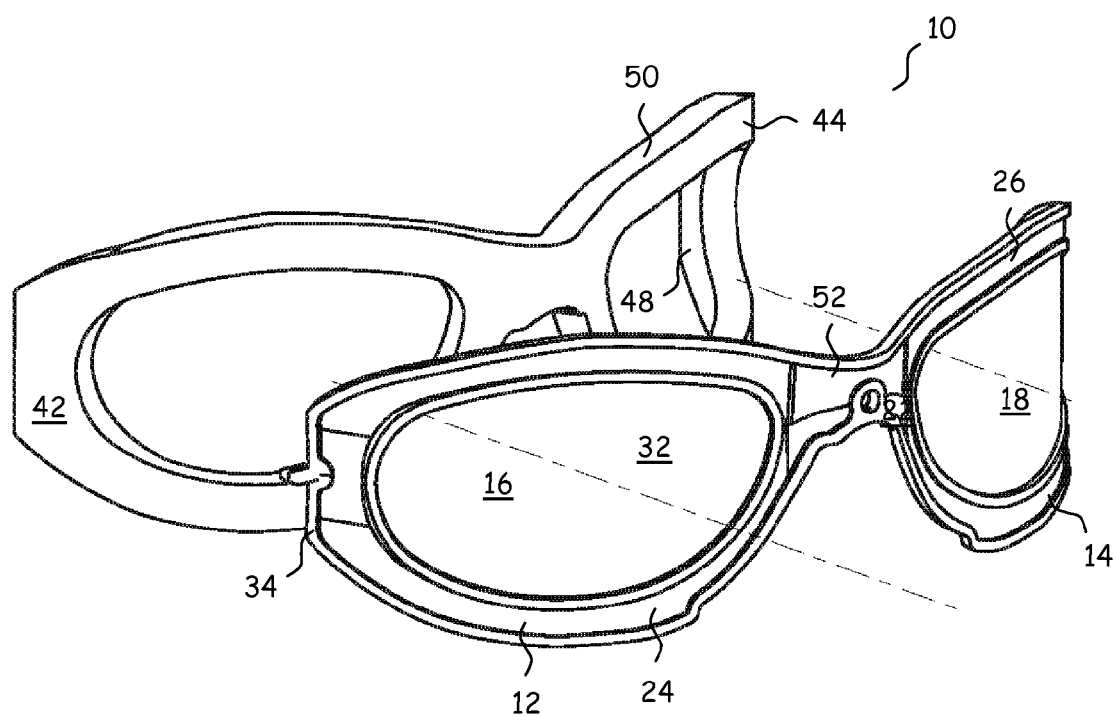
Figure 13:
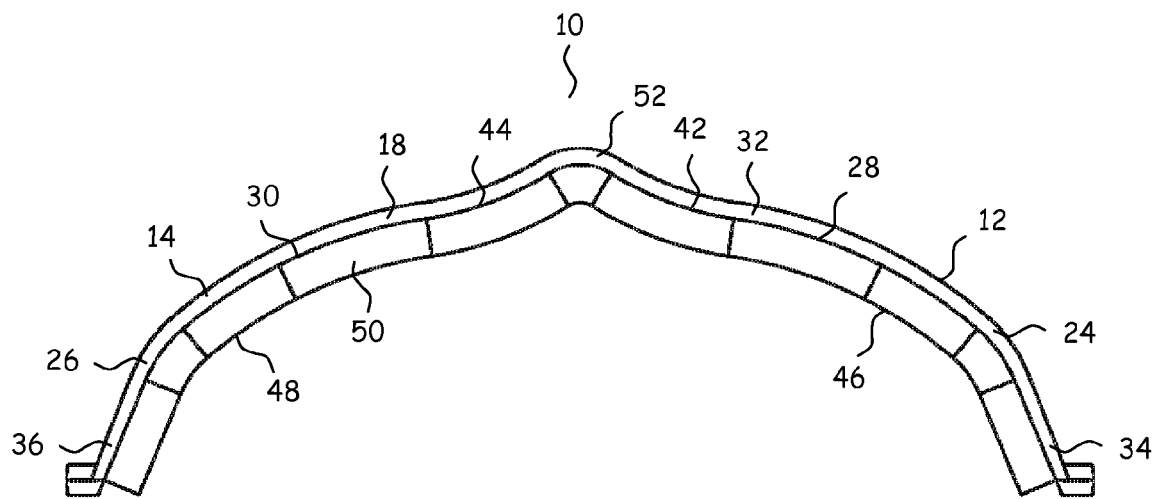
FIG. 13 is a top view of the set of eye pieces shown in FIG. 8.
Figure 14:
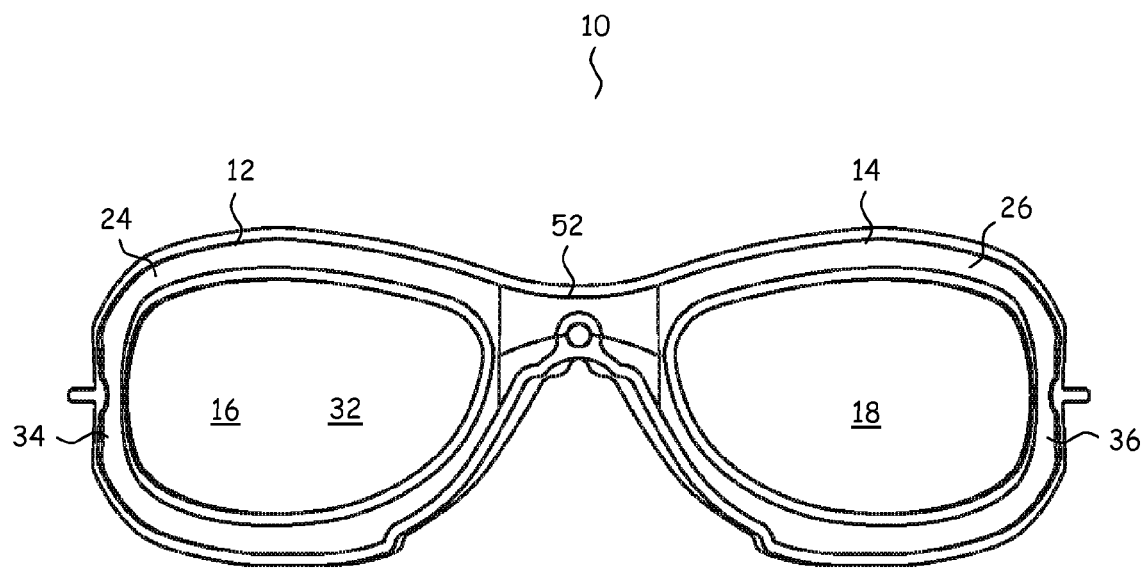
FIG. 14 is a front view of the set of eye pieces shown in FIG. 8, FIG. 15 schematically shows a perspective view of a human's head with yet another exemplary new set of eye pieces, FIG. 16 schematically shows the human's head from the side with the new set of eye pieces of FIG. 15, FIG. 17 schematically shows an exploded perspective view of the set of eye pieces of FIG. 15 behind video goggles with an IR camera, FIG. 18 schematically shows a perspective view of the set of eye pieces of FIG. 15 behind video goggles with an IR camera, FIG. 19 schematically shows an exploded perspective view of the set of eye pieces of FIG. 15.
Figure 15:
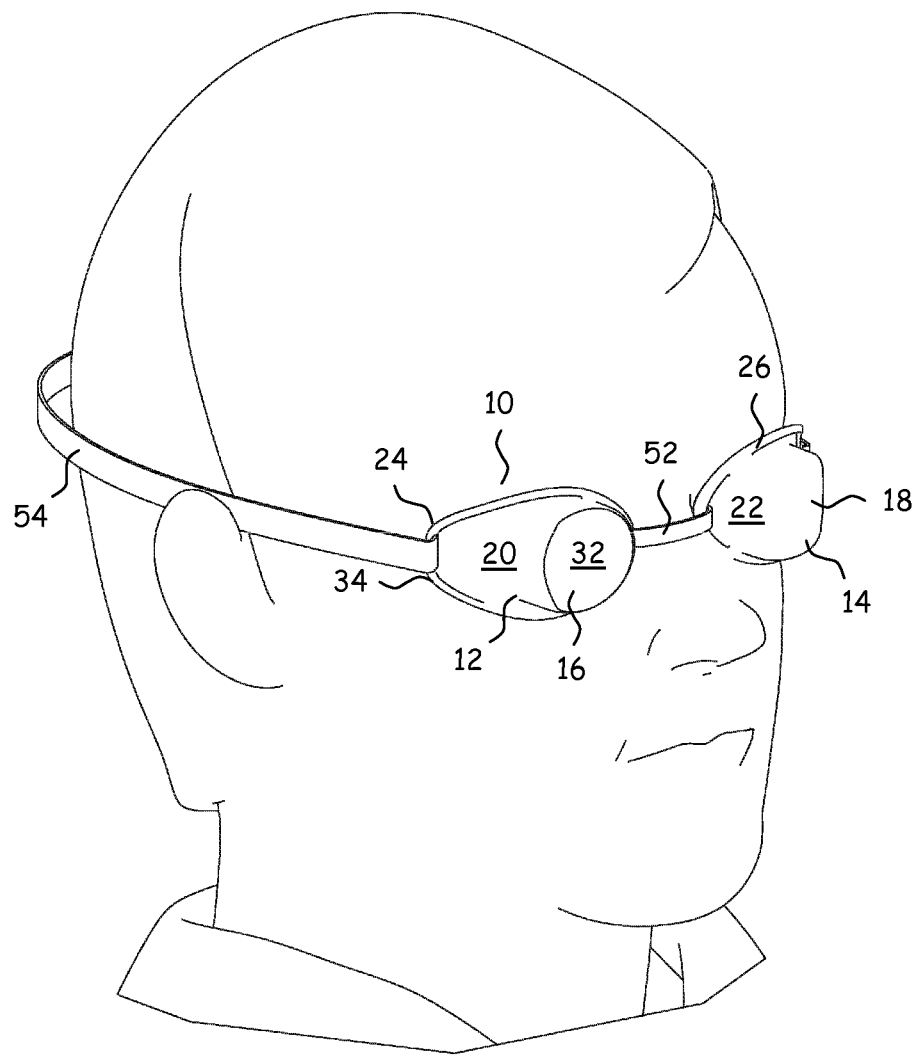
Figure 16:
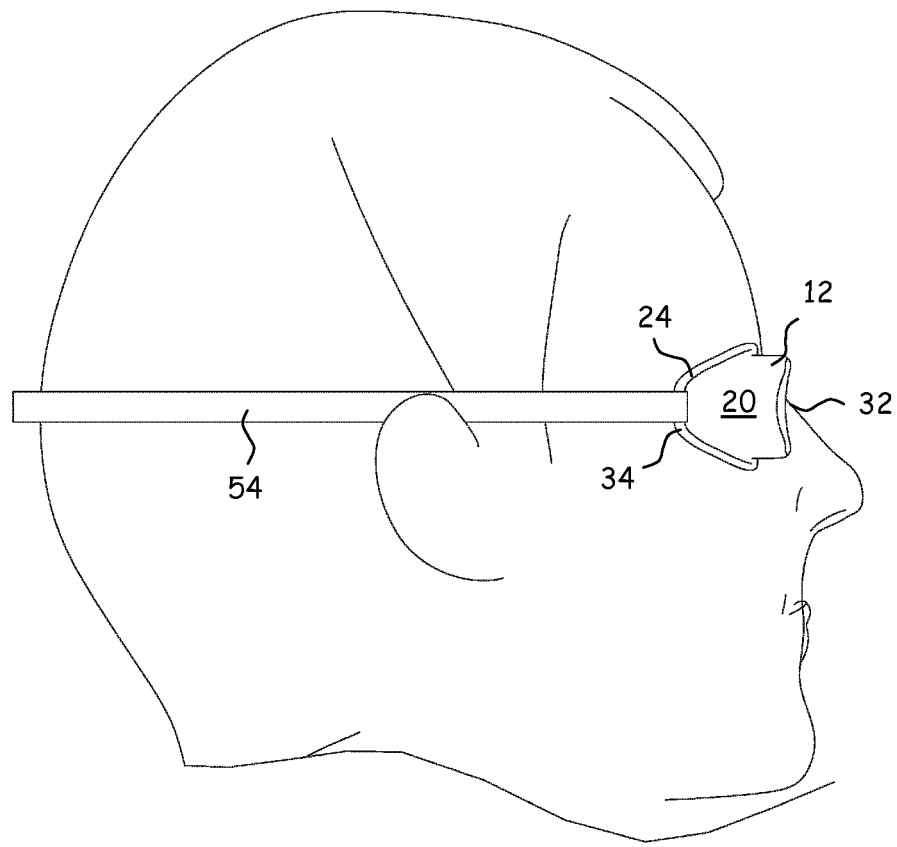
Figure 17:
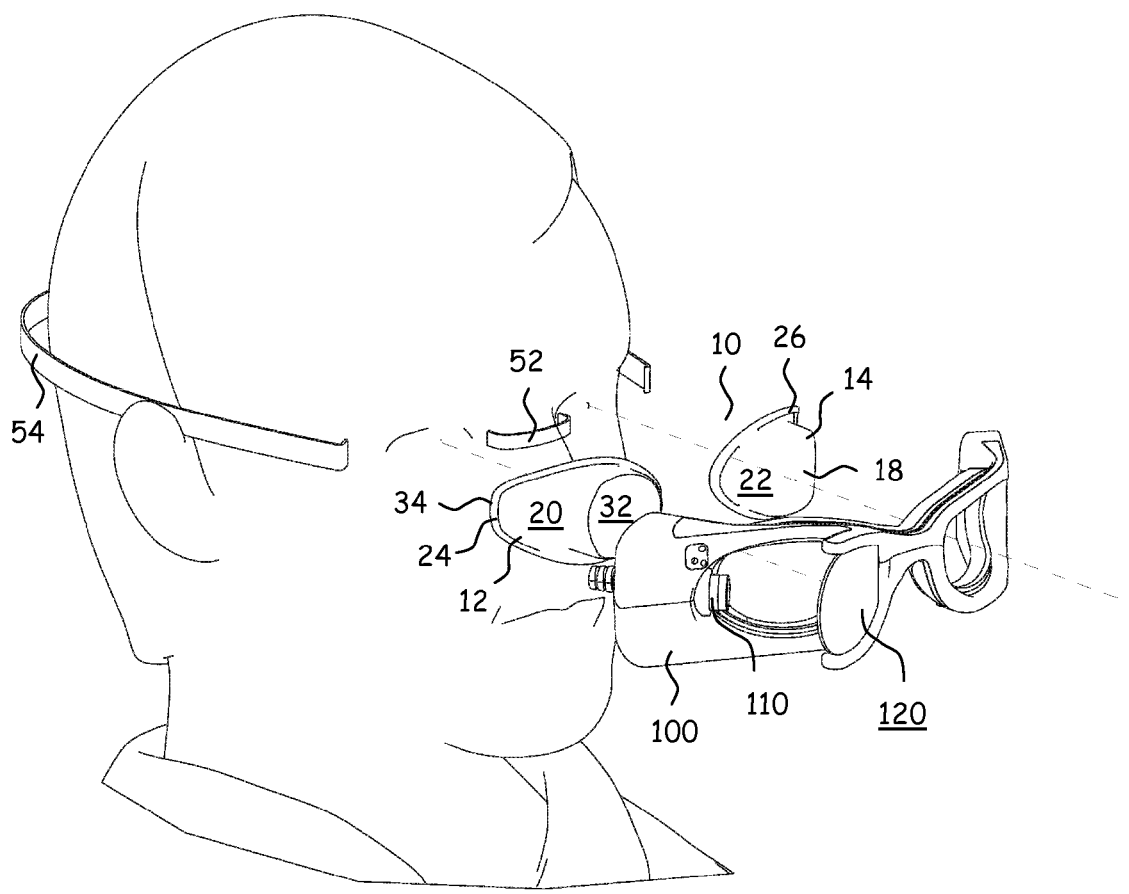
Figure 18:
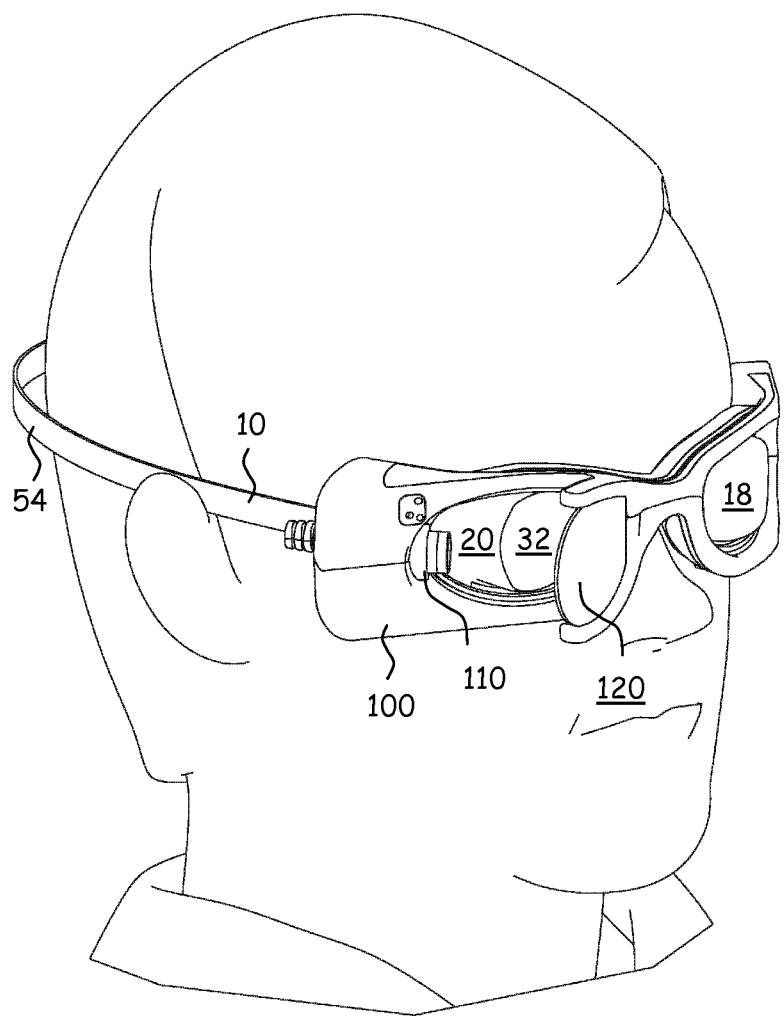
Figure 19:
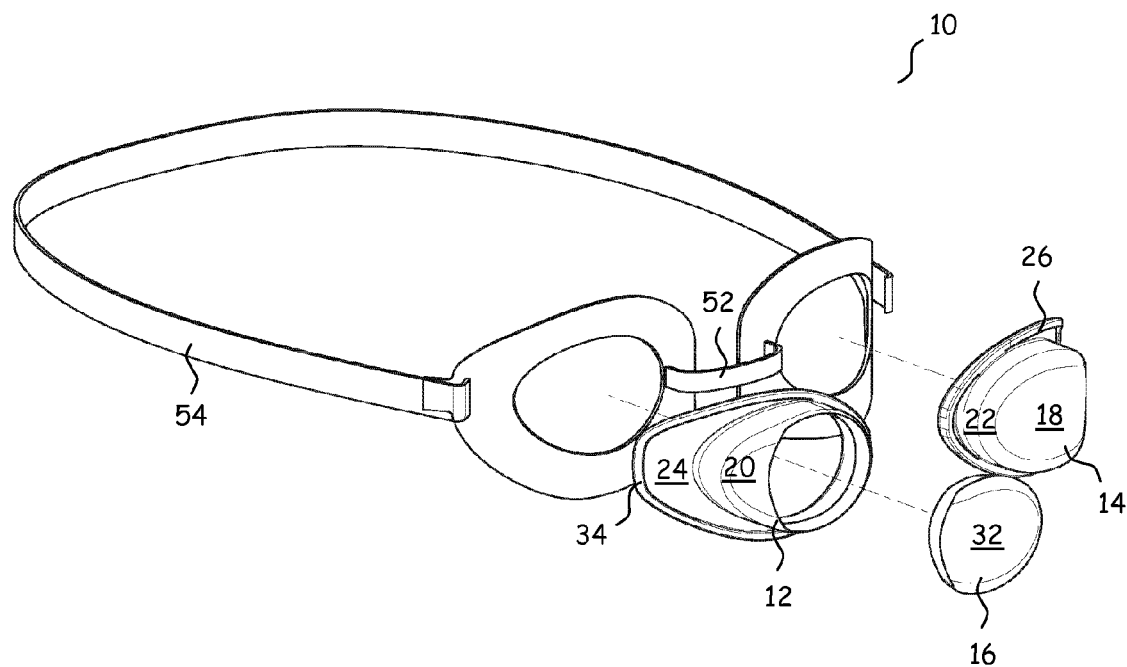
Figure 20:
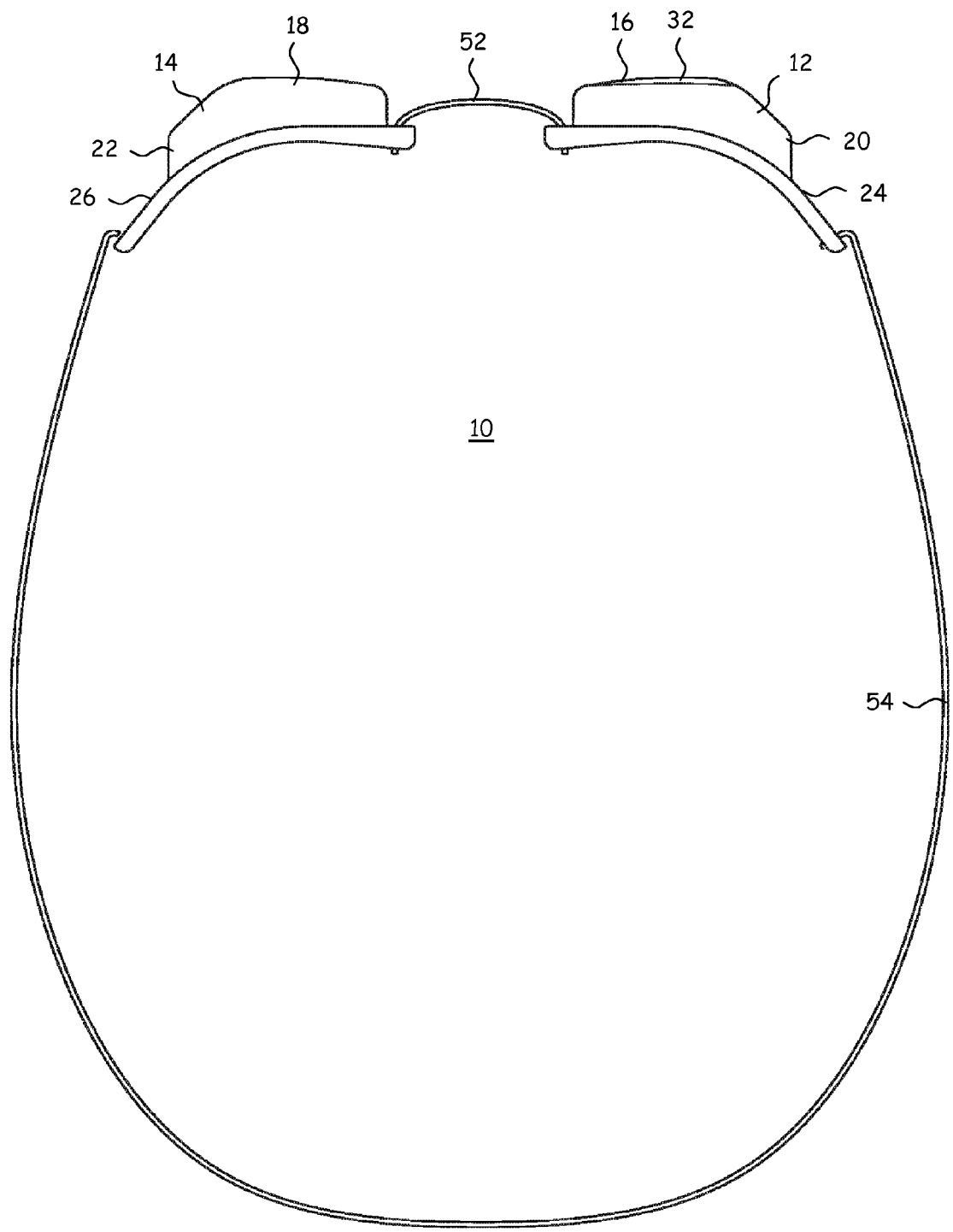
FIG. 20 is a top view of the set of eye pieces shown in FIG. 15.
Figure 21:
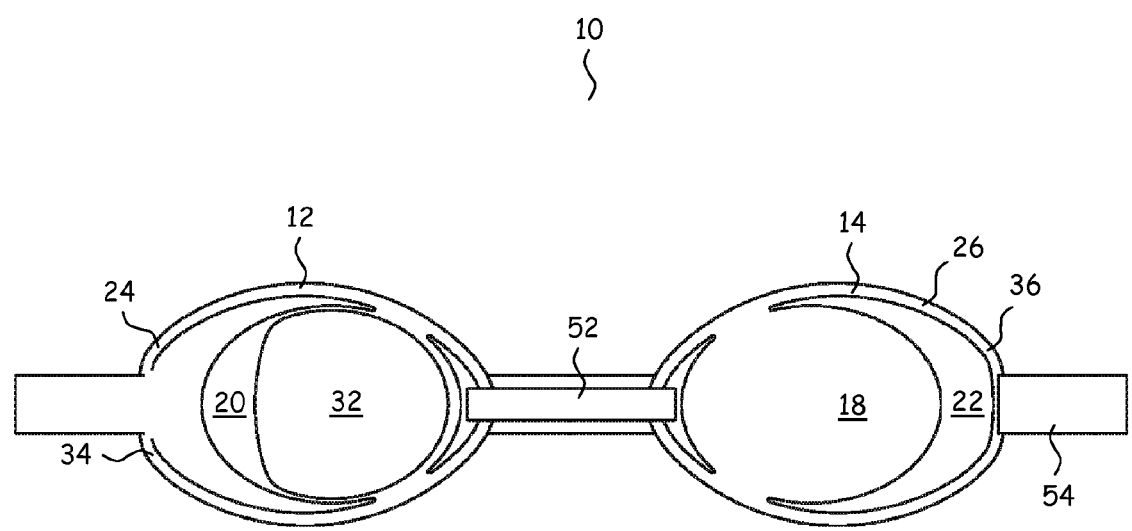
FIG. 21 is a front view of the set of eye pieces shown in FIG. 15.

To assist in retaining the eye pieces 12, 14 against the face of the human, each of the illustrated eye pieces 12, 14 has an adhesive layer in the form of the illustrated adhesive tape layers 38, 40, overlaying the respective posterior surfaces 28, 30, see FIG. 6. Each adhesive tape layer 38, 40 can be conventional "double-sided" or "double-coated" tape having a first adhesive surface 42, 44 secured to the respective posterior surface 28, 30 of the respective eye piece 12, 14, and a second adhesive surface 46, 48 that is placed against the skin of the human. Each eye piece 12, 14 can include a removable, protective cover layer (not shown) overlaying the second adhesive surface 46, 48 of the tape to protect the second adhesive surface from adhering to extraneous matter prior to use.

The eye pieces 12, 14 can be provided with two separate pieces of double-sided adhesive tape that are shaped to be applied to the posterior surfaces 28, 30 of the eye pieces 12, 14 and a set of instructions for informing a human how to apply the tape to the eye pieces.

The second adhesive surfaces 46, 48 desirably exhibits a bonding strength suitable to adhere the eye pieces 12, 14 to the skin of the human during normal conditions of use, yet allows the eye pieces 12, 14 to be removed with minimal discomfort. The first adhesive surfaces 42, 44 of the tape desirably provide a bonding strength sufficient to prevent separation of the tape from the eye pieces 12, 14 during normal conditions of use and during removal of the eye pieces.

In some embodiments of the new apparatus 10 with the first and second eye pieces 12, 14, the double sided tape is discarded before use of the eye pieces by another human, in which case, the first adhesive surfaces 42, 44 also allows the tape to be peeled away from the posterior surfaces 28, 30 of the eye pieces 12, 14 to permit replacement of the tape, when the apparatus 10 with the first and second eye pieces 12, 14 has been removed from the human after use, and subsequently will be used again by the same or another human.

The posterior surfaces preferably include a layer of a flexible material, such as polyethylene foam, to provide a sealing surface that better accommodates uneven facial surfaces. The flexible material may be included in the adhesive tape. The adhesive may form a layer of an adhesive tape, such as MSX-6674C which is a double coated synthetic rubber/gentle acrylic adhesive tape designed for medical applications supplied by 3M Medical Specialties.

In some embodiments, a layer of a suitable adhesive (e.g., acrylic) can be formed directly on the posterior surfaces 28, 30 of the eye pieces 12, 14.

Preferably, the new apparatus 10 of this type is discarded after removal from the human, whereby a need of proper cleaning of the eye pieces between uses by different humans is eliminated.

Not having a head band and a nose piece or nose strap for interconnecting the eye pieces 12, 14, facilitates individual lightproof positioning of each eye piece across the respective eye, since each eye piece can be freely oriented and applied to the face of the human independent of the orientation and positioning of the other eye piece.

FIG. 3 is a schematic exploded view of an assembly of the new apparatus 10 with the first and second eye pieces 12, 14 and video goggles 100.

Figure 4:
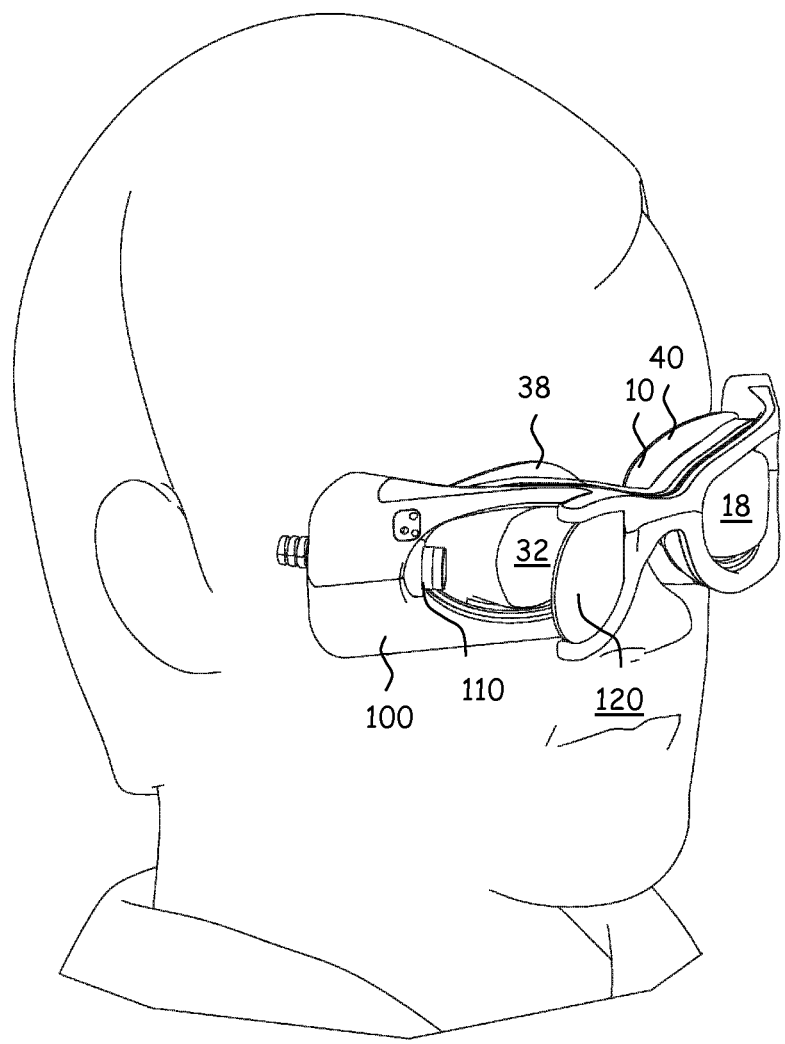
Figure 5:
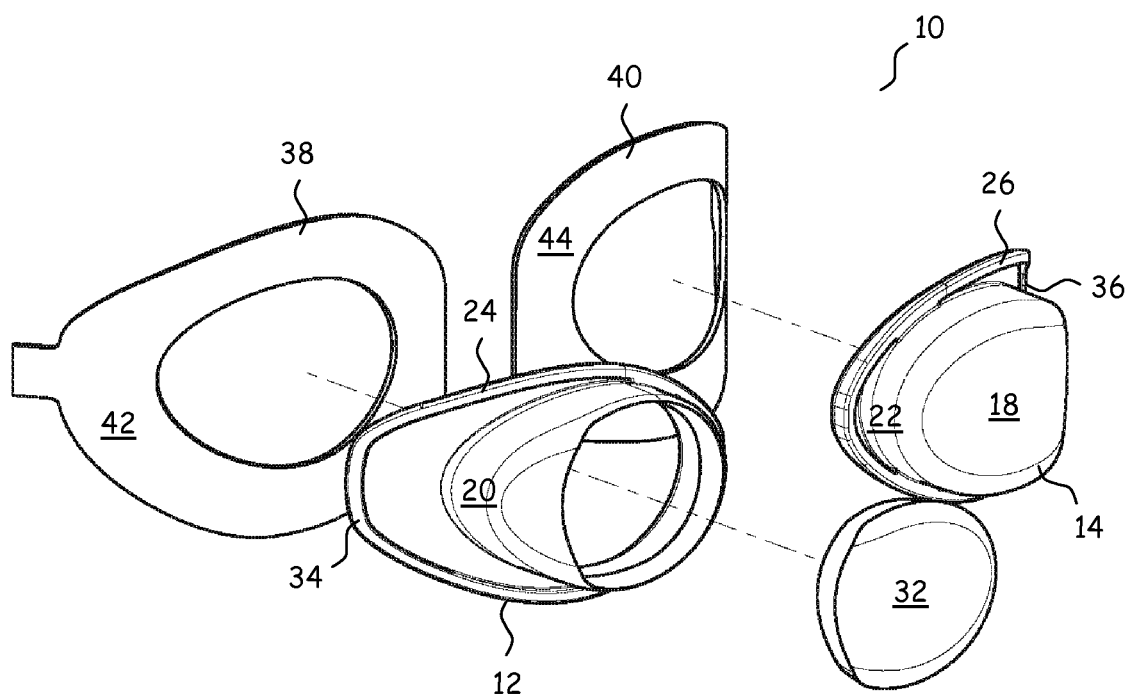

FIG. 4 shows the assembly in its intended operational position mounted on the human's head.

The apparatus 10 with the first and second eye pieces 12, 14 is worn by the human underneath the separate video goggles 100. The video goggles 100 have an infrared camera 110 for observation of right eye movements, such as nystagmus. The video goggles 100 also comprise infrared light diodes (not shown) for illumination of the right eye with infrared light. The right eye piece 12 has a region 32 that is transparent for infrared light and opaque to visible light. The infrared light reflected from the right eye is deflected by the mirror 120 and recorded by the infrared camera 110.

Since darkness is provided by the apparatus 10 with the first and second eye pieces 12, 14, the separate video goggles 100 need not be opaque to visible light and in particular do not need to provide a lightproof seal around the eyes of the human, making it much easier to fit the video goggles 100 to humans with different facial anatomy. This also reduces the effort of cleaning the video goggles between uses.

FIGS. 8-14 illustrate another apparatus 10 comprising right and left eye pieces 12, 14, each of which having a construction that is similar to the construction of the eye pieces 12, 14 of the apparatus 10 shown in FIGS. 1-7 except for the facts that apparatus 10 illustrated in FIGS. 15-21 includes a nose piece 52 that interconnects the adjacent nasal ends of eye pieces 12, 14, and that a flexible member 50 substitutes the double sided adhesive tape.

The illustrated right eye piece 12 and left eye piece 14 and nose piece 52 are manufactured in one piece forming a one-piece unit.

Like the apparatus 10 shown in FIGS. 1-7, the eye pieces 12, 14 have adhesive surfaces for attachment to the skin surface around the respective eyes of the human.

The adhesive surfaces 46, 48 intended for attachment to a skin surface are formed on the flexible member 50, e.g. made of foam or rubber, to provide a sealing surface that is capable of accommodating uneven facial surfaces. The flexible member 50 has a thickness that provides a distance between the eye pieces 12, 14 and the respective eyes so that the illustrated apparatus 10 with the first and second eye pieces is comfortable to wear.

The flexible member 50 has first adhesive surfaces 42, 44 adhering to posterior surfaces 28, 30 of the respective eye pieces 12, 14 and second adhesive surfaces 46, 48 for adhering to a skin surface of the human's face.

Like the apparatus 10 shown in FIGS. 1-7, the right eye pieces 12 has a region that is transparent for infrared light, e.g. for observation of eye movements, such as nystagmus, by an infrared camera.

A similar apparatus (not shown) with the first and second eye pieces is also provided that has a construction that is similar to the apparatus 10 shown in FIGS. 8-14 except for the fact that the similar apparatus does not have adhesive surfaces. Instead, the similar apparatus are kept in place in its operating position by the worn video goggles abutting and pressing the apparatus with the first and second eye pieces against the skin surface of the human.

FIGS. 15-21 illustrate yet another apparatus with the first and second eye pieces 12, 14, which comprises right and left eye pieces 12, 14, respectively, that have a construction that is similar to the eye pieces 12, 14 of apparatus 10 shown in FIGS. 1-7 except for the fact that apparatus 10 illustrated in FIGS. 8-14 includes a nose strap 52 that interconnects the adjacent nasal ends of flanges 24, 26 and an elastic head strap 54 that is connected to the temporal end portions of flanges 24, 26 and extends around the rear of the head. In this embodiment, the adhesive layer 46, 48 is not needed since the nose strap 52 and head strap 54 cooperate to firmly retain the eye pieces 12, 14 on the head. Like the apparatus 10 shown in FIGS. 1-7, the right eye pieces 12 has a region that is transparent for infrared light, e.g. for observation of eye movements, such as nystagmus, by an infrared camera.

Figure 22:
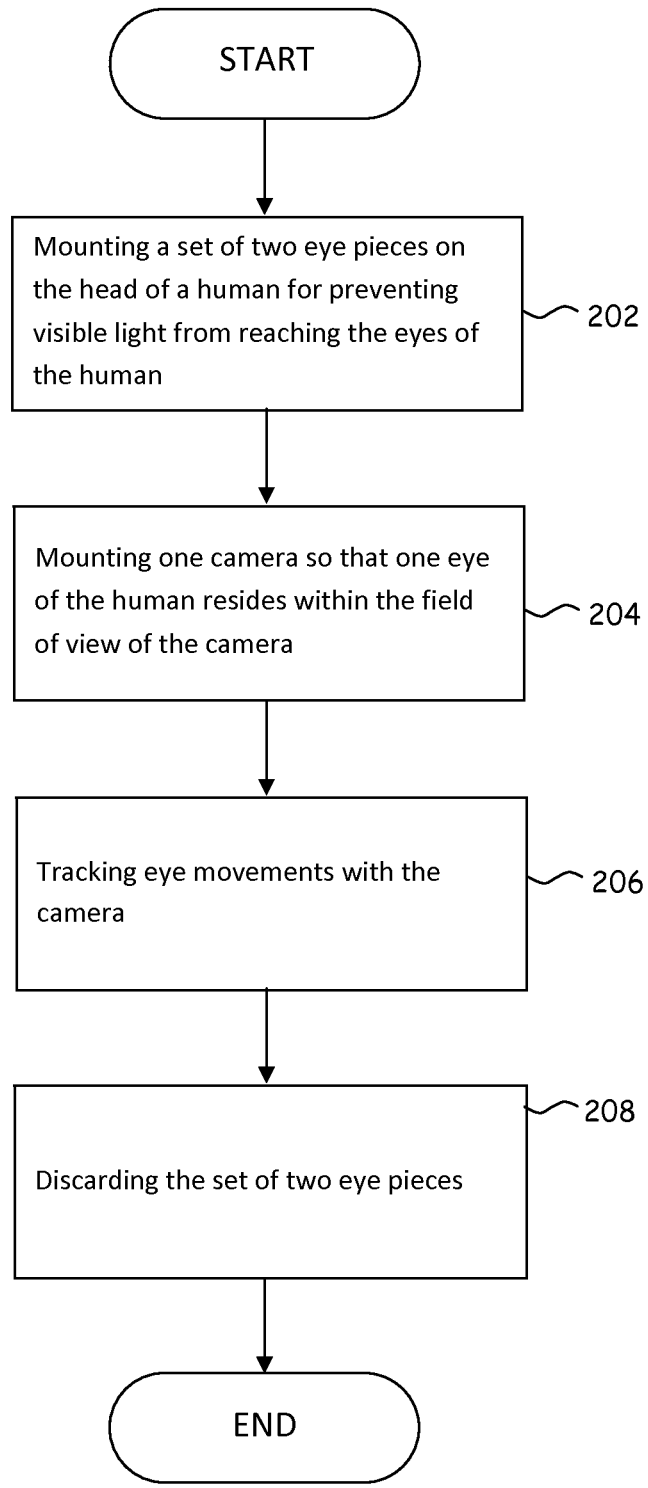
FIG. 22 is a flowchart of the new method.

FIG. 22 shows a flowchart of the new method 100 comprising the steps of:
202: Mounting an apparatus with the first and second eye pieces as disclosed above on the head of a human for preventing visible light from reaching the eyes of the human,
204: Mounting one camera so that one eye of the human resides within the field of view of the camera,
206: Tracking eye movements with the camera, and
208: Discarding at least part of the apparatus with the first and second eye pieces, preferably the apparatus with the first and second eye pieces.

When mounting the apparatus with the first and second eye pieces 12, 14, the human first opens his or her eyes wide so as to expand the orbicularis oculi muscles, positions the eye pieces 12, 14 over the eyes as previously described, and presses the eye pieces 12, 14 against the face so as to ensure a good bond between the respective adhesive surfaces 46, 48 and the skin. Pressing the eye pieces against the face tends to create a small vacuum between the eyes and the eye pieces. This vacuum assists in retaining the eye pieces 12, 14 against the face during use. When the eye pieces 12, 14 are properly positioned, the orbicularis oculi muscles can be relaxed.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus for covering a left eye and a right eye of a human, comprising:
    a first eye piece configured for covering a left eye of a human; and
    a second eye piece configured for covering a right eye of the human;
    wherein the first eye piece and the second eye piece are configured for preventing transmission of visible light;
    wherein at least one of the first eye piece and the second eye piece comprises a region that is transparent for electromagnetic radiation with a wavelength range outside a visible range; and
    wherein the region that is transparent for electromagnetic radiation with the wavelength range outside the visible range is made of a material that is transparent for visible light coated with a material that is opaque to visible light.

2. The apparatus according to claim 1, wherein the first eye piece and the second eye piece are unconnected for individual and independent positioning at the respective left and right eyes.

3. The apparatus according to claim 1, at least one of the first eye piece and the second eye piece comprises an adhesive surface for adhesively securing the at least one of the first eye piece and the second eye piece to a skin surface of the human.

4. The apparatus according to claim 3, wherein the adhesive surface is on a flexible material.

5. The apparatus according to claim 3, wherein the adhesive surface comprises a layer of adhesive tape that is secured to the at least one of the first eye piece and the second eye piece.

6. The apparatus according to claim 5, wherein the adhesive surface is a part of a double-sided tape, the double-sided tape having an additional adhesive surface adhering to a posterior surface of the at least one of the first eye piece and the second eye piece.

7. The apparatus according to claim 1, wherein the region that is transparent for electromagnetic radiation with the wavelength range outside the visible range comprises at least a portion of a surface that covers the left eye or the right eye.

8. The apparatus according to claim 1, wherein the at least one of the first eye piece and the second eye piece with the region that is transparent for electromagnetic radiation with the wavelength range outside the visible range, comprises a frame with an aperture for accommodation of a window that defines the region, the frame being made of a material that is different from a material of the window.

9. The apparatus according to claim 1, wherein at least one of the first eye piece and the second eye piece comprises a peripheral flange that is shaped to conform to a shape of an orbital rim of the left eye or the right eye.

10. The apparatus according to claim 1, wherein at least one of the first eye piece and the second eye piece comprises a transversal portion that is positioned in front of one of the eyes when worn by the human, and an annular peripheral wall that surrounds the transversal portion and extends rearwardly therefrom, and a peripheral flange surrounding the peripheral wall and shaped to conform to a shape of an orbital rim of one of the eyes.

11. The apparatus according to claim 1, further comprising a nose piece that interconnects the first eye piece and the second eye piece, and that is configured for fitting across a nose of the human.

12. The apparatus according to claim 11, further comprising a head strap that interconnects the first eye piece and the second eye piece, and that is configured for fitting around a rear of a head of the human.

13. The apparatus of claim 12, wherein at least one of the first eye piece and the second eye piece comprises a peripheral flange that is shaped to conform to a shape of an orbital rim of the left eye or the right eye.

14. The apparatus of claim 11, wherein at least one of the first eye piece and the second eye piece comprises a peripheral flange that is shaped to conform to a shape of an orbital rim of the left eye or the right eye.

15. The apparatus according to claim 1, wherein the region has a transmittance of more than 50% of infrared light in a wavelength range from 850-1100 nm.

16. A device for worn above a shoulder of a user, comprising:
    a structure;
    at least one camera coupled to the structure; and
    the apparatus of claim 1;
    wherein the first eye piece and the second eye piece of the apparatus are coupled to the structure.

17. The device according to claim 16, wherein the structure comprises a helmet.

18. The device according to claim 16, wherein the structure comprises a mask.

19. The device according to claim 16, wherein the structure comprises a frame of a glasses or goggles.

20. A method of determining an eye movement, comprising:
    providing an apparatus having a first eye piece a second eye piece, and a camera, wherein at least one of the first eye piece and the second eye piece comprises a region that is transparent for electromagnetic radiation with a wavelength range outside a visible range, wherein the region that is transparent for electromagnetic radiation with the wavelength range outside the visible range is made of a material that is transparent for visible light coated with a material that is opaque to visible light;
    preventing visible light from reaching eyes of a human using the first eye piece and the second eye piece; and
    tracking a movement of at least one of the eyes using the camera.

* * * * *